United States Patent [19]

Preuss

[11] Patent Number: 4,519,949
[45] Date of Patent: May 28, 1985

[54] STEROID-20-CARBOXYLIC ACID COMPOUNDS AND A PROCESS FOR THEIR PRODUCTION

[75] Inventor: Wolfgang Preuss, Monheim, Fed. Rep. of Germany

[73] Assignee: Henkel Kommanditgesellschaft auf Aktien, Duesseldorf, Fed. Rep. of Germany

[21] Appl. No.: 423,276

[22] Filed: Sep. 24, 1982

Related U.S. Application Data

[63] Continuation-in-part of Ser. No. 262,971, May 12, 1981, abandoned.

[30] Foreign Application Priority Data

May 16, 1980 [AT] Austria ................... 2629/80

[51] Int. Cl.³ .................................. C07J 9/00
[52] U.S. Cl. .................. 260/397.1; 260/397.3
[58] Field of Search ............... 260/397.1, 397.3

[56] References Cited

U.S. PATENT DOCUMENTS 4,252,730  2/1981  Krbechek ............... 260/397.3

Primary Examiner—Elbert L. Roberts
Attorney, Agent, or Firm—Ernest G. Szoke; Nelson Littell, Jr.

[57] ABSTRACT

New Δ1,4,9(11)-pregnatrien-3-one-2o-carboxlic acid compounds are described, corresponding to general formula I below:

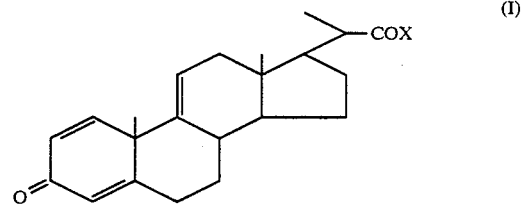

in which X represents halogen, particularly chlorine or bromine or $NH_2$. There is also described the process for producing compounds corresponding to general formula I by dehydrating the corresponding saturated starting compounds hydroxylated in the 11-position to form the 9(11)-ene-bond, after which the product obtained is, if desired, subjected to chemical transformation into the end products corresponding to general formula I. In particular, it is possible to carry out formation of the 20-acid halides and dehydration in the 9(11)-position in a single process step.

11 Claims, No Drawings

STEROID-20-CARBOXYLIC ACID COMPOUNDS AND A PROCESS FOR THEIR PRODUCTION

This is a continuation-in-part of Ser. No. 262,971, filed May 12, 1981, now abandoned.

BACKGROUND OF THE INVENTION

European Patent Application No. 004913 as laid open describes inter alia a process for the production of 17-C-steroid-α-propionic acid compounds, particularly 3-oxo-pregna-4-ene-20-carboxylic acid (Δ4-BNC) and/or 3-oxo-pregna-1,4-diene-20-carboxylic acid (Δ1,4-BNC), by microbial side chain degradation on 17 C-side chain steroid substrates. By using microorganism defect mutants grown and selected in a certain manner, which give steroid compounds containing the 17 C-α-propionic acid residue even in the absence of inhibitors which inhibit degradation of the steroid ring and/or growth inhibitors, it is possible to obtain Δ4-BNC and, in particular, Δ1,4-BNC in commercial quantities. Another embodiment of this process is described in European Patent Application No. 0015308.

These Δ1,4-BNC compounds formed by the side chain degradation of natural sterol compounds contain a functional group in only the 3-position of the ring system. However, all pharmacologically active corticosteroids contain additional oxygen functions and, in some cases, other functional groups in the molecule. The 9,11,17 and 21 positions are particularly important in this respect. Normally some of the oxygen functions are chemically introduced, including in particular the 17 and 21 positions.

By contrast, oxidation of the 11-position in steroid compounds is preferably carried out microbially. Several such microbial steroid oxidation processes are described in the specialist literature. In this connection, reference is made to the following publications and to the original Articles quoted therein: F. Drawert "Biosynthese von Hydroxy-Verbindungen (Biosynthesis of Hydroxy Compounds)"; Houben-Weyl "Methoden der organischen Chemie" (1978) 6/1d, pages 378 to 388; T. H. Stoudt, Adv. Appl. Microbiol. 2 (1960), pages 190 to 195; and W. Charney and H. L. Herzog "Microbial Transformations of Steroids" Academic Press (1967), New York, page 29.

Certain BNC-compounds containing an oxygen function in the 11-position and, in particular, 11-hydroxyl groups are described in German Offenlegungsschrift No. 28 39 033. This Offenlegungsschrift describes inter alia 11 α- and 11 β-hydroxy-Δ1,4-BNC and their production. It also describes the dehydration of these compounds to form the corresponding BNC compounds containing an additional double bond in the 9(11)-position. This dehydration process may be carried out in known manner, for example by converting the 11-hydroxyl compounds by reaction with methane sulfonic acid chloride or p-toluene sulfonic acid chloride into the corresponding sulfonic acid esters and converting the acid esters thus obtained into the corresponding Δ9(11)-steroids by treatment with weak bases, such as sodium acetate. However, dehydration may also be carried out by heating the above-mentioned starting compounds with mineral acids, for example sulfuric acid, phosphoric acid or hydrochloric acid, in an inert solvent, such as benzene, toluene or xylene.

European Patent Application No. 11235, which is not a prior publication, describes 9-hydroxylated BNC-compounds and a process for their production. The description relates in particular to 9α-hydroxy-pregna-4,17(20)-diene-3-one-20-carboxylic acid.

9α-OH-Δ4-BNC is described in U.S. Pat. No. 4,062,880 which also mentions the transformation of its methyl ester into the ester of Δ4,9(11)-BNC by dehydration.

OBJECTS OF THE INVENTION

The object of the present invention is to provide new steroid carboxylic acids and corresponding carboxylic acid derivatives containing a carboxyl group function in the 20-position which contain an additional double bond in the 9(11)-position. Accordingly, the invention seeks to provide new valuable steroid compounds which are also particularly suitable for use as intermediate products for the production of pharmacologically active steroid compounds.

DESCRIPTION OF THE INVENTION

In a first embodiment, therefore, the present invention relates to new Δ1,4,9(11)-pregna-3-one-20-carboxylic acid compounds containing a double bond in the 1(2)-position and corresponding to general formula I below

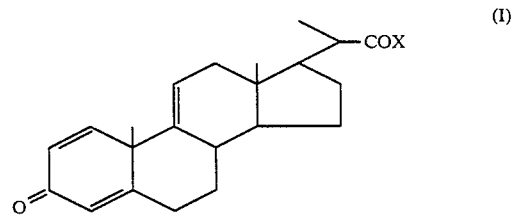

(I)

in which X has one of the following meanings: halogen or $NH_2$. The halogens of particular significance are bromine and, more particularly, chlorine.

Accordingly, the invention provides new BNC compounds which are olefinically unsaturated at least 3 times, which have the 1,4-diene-3-one structure in the A-ring of the steroid system, which contain in the 20-position a carboxylic acid halide group or a carboxylic acid amide group, which additionally contain an olefinic double bond in the 9(11)-position.

It has also been found in accordance with the present invention (and this is another subject of the present invention) that the new 9(11)-unsaturated compounds may readily be obtained from the structurally similar preliminary compounds which are saturated in the 9(11)-position and carry a hydroxyl group in the 11 position. The hydroxyl group in the 11-position can be present in the α- or β-position. The 11β-position is preferred. If starting compounds of this type are subjected to dehydration, water may be split off in the 9(11)-position and the olefinic bond required in accordance with the invention simultaneous formed in that position.

The starting compounds for the process according to the invention are described in my copending, commonly-assigned U.S. patent application Ser. No. 262,965, filed May 12, 1981, now abandoned in favor of Ser. No. 407,790, filed Aug. 13, 1982. Their dehydration to form the compounds of formula I according to the invention is preferably carried out using dehydrating agents at normal or only moderately elevated temperatures. Temperatures of up to at most around 80° C. are particularly preferred. In particular, it may be desirable not to exceed temperatures of the order of 50° C. It can be of particular advantage to work at temperatures in the range from −10° to +25° C.

Any known chemical dehydrating agents for eliminating water from secondary or tertiary alcohols are suitable for carrying out the process according to the invention providing they do not enter into undesirable secondary reactions with the starting material. Acid dehydrating agents, particularly corresponding mineral acids, for example sulfuric acid, phosphoric acid or hydrochloric acid, or mineral acid derivatives may be used with advantage. It is also possible to apply a treatment with N-halogen amides or N-halogenimides and $SO_2$, as described in British Pat. No. 869,815. The compounds to be dehydrated may be dissolved in inert solvents, for example hydrocarbon compounds.

One particularly important aspect of the invention concerns compounds corresponding to general formula I, in which X is halogen, particularly chlorine, and their production. These acid halides are for example important intermediate products for subsequent chemical reactions involving transformation of the substituent in the 17-position of the steroid skeleton. The 9(11)-ene-20-carboxylic acid halides which are required in accordance with the invention may surprisingly be formed under extremely mild reaction conditions under which there is no undesirable co-reaction of other reactive sites of the parent polyunsaturated BNC-structure.

In one preferred embodiment of the process according to the invention, dehydration to form the 9(11)-ene bond may be combined with formation of the 20-carboxylic acid halide. In this case, it has been found that the use of standard halogenating agents, particularly thionyl halide, in excess together with a tertiary N-base may lead directly to the formation of the 9(11)-unsaturated 20-carboxylic acid halide from the corresponding 9- and 11-hydroxy-20-carboxylic acids. The carboxylic acid halide formed may then either be readily hydrolysed to form the free acid, reacted with alcohols of the type mentioned to form the corresponding esters or converted with ammonia or an ammonia-yielding compound into the carboxylic acid amide. The various new compounds according to the invention may be conveniently obtained in this way.

As already mentioned, the 9(11)-ene-20-carboxylic acid halides required in accordance with the invention are surprisingly formed under such mild reaction conditions that there is no undesirable co-reaction of other reactive sites of the parent polyunsaturated BNC structure. Thus, it has been found that for example substantially quantitative dehydration accompanied by acid chloride formation takes place when the following reaction conditions are applied: reaction temperatures below 15° C., working in the presence of an inert diluent and in the presence of a basic compound. Suitable inert diluents or solvents are, for example halogenated hydrocarbons or—with certain reservations—ethers. Suitable inert solvents are, for example, methylene chloride or chloroform. The basic compounds used may be above all a tertiary N-base, particularly pyridine or dimethyl formamide, best employed in quantities of at least 2 moles and preferably at least 3 moles per mole of steroid carboxylic acid.

In the embodiment which has just been described (simultaneous dehydration and formation of the carboxylic acid halide group), the halogenating agent is used in an excess over and above the quantity required for forming the carboxylic acid halide group. In general, the halogenating agent is used at least in an approximately 1-molar excess. In addition, it can be of advantage to avoid too large an excess. The excess in which the halogenating agent is used is preferably in the 1- to 3-molar range and preferably in the 1- to 1.5-molar range. Suitable halogenating agents are phosphorus halides, particularly $PCl_3$ or $PCl_5$, and the corresponding bromides, but above all thionyl halide and, in particular, thionyl chloride. The halogenating agent is best added to the solution of the steroid compounds to be reacted in the inert solvent. It has been found to be of advantage to use the halogenating agent in the purest possible form. Any impurities present in the halogenating agent obviously promote undesirable secondary reactions. The halogenating agent is best purified for example with an unsaturated compound, such as linseed oil or, in particular, squalene. These unsaturated components react with the impurities in the halogenating agent and thus reduce the formation of undesirable secondary products to a minimum.

In cases where 9(11)-unsaturated carboxylic acids within the scope of general formula I are already present as starting materials for forming the carboxylic acid halides, formation of the corresponding acid halides, particularly the corresponding acid chloride, may be carried out in the same way as described above. In this connection, however, it can be of advantage to use only a very limited excess of the halogenating agent preferably amounting to no more than 20 mole percent and, more particularly, to no more than 10 mole percent. Particularly suitable reaction conditions for a reaction such as this are: reaction temperatures below 10° C., preferably below 5° C., stoichiometric quantities of the reactants or only a very limited excess of the halogenating agent (particularly thionyl chloride) which best does not exceed the limits indicated above and short reaction times which preferably do not exceed 30 minutes. The following combination of reaction conditions may be particularly suitable: 0° C., thionyl chloride excess of 0 to 10 mole percent and a reaction time of 15 to 20 minutes in the presence of an inert solvent. In the case described here, there is no need to add either a catalyst (for example pyridine or dimethyl formamide) or any significant amount of base, such as for example tertiary amine or alkali carbonate.

The new carboxylic acid amides of general formula I according to the invention may be obtained from the acid halides by reacting the 20-carboxylic acid halide with ammonia or with an ammonia-yielding compound. This reaction is best carried out at temperatures in the range from about −20° C. to about 80° C. and preferably at temperatures in the range from about −5° C. to about 35° C. The ammonia or the compound which yields ammonia under the reaction conditions is used in at least substantially equimolar quantities. Suitable quantities in which to use the ammonia or the ammonia-yielding compound are for example from 1.1 to 5 equivalents (based on acid halide) and preferably from about 1.2 to about 3 equivalents. If an ammonia-yielding compound is used rather than ammonia itself, ammonium hydroxide is particularly suitable for this purpose.

Reaction of the 20-carboxylic acid halide with ammonia or the ammonia-yielding compound is again preferably carried out in an organic solvent, for example in halogenated hydrocarbons, as mentioned above. In this case, too, a particularly suitable inert solvent is methylene chloride or chloroform.

If ammonium hydroxide is used as the ammonia-yielding compound, an aqueous phase accumulates in addition to the organic phase in the reaction mixture. The reaction product may be recovered by simple phase separation or even by separating off the amide precipitated in solid form. The organic phase separated off is best repeatedly washed with water, subsequently dried, for example with calcium sulfate, and filtered. The organic solvent used as the inert diluent is separated off, after which the carboxamido compound may be further purified in known manner.

Any hydrohalic acid which is given off during the reaction between the carboxylic acid halide and the ammonia may be bound by an excess of ammonia or ammonium hydroxide, although a basic component may also be used for binding the acid liberated.

The new compounds corresponding to general formula I are valuable products of steroid chemistry and, more particularly, are important intermediate products in the production of pharmacologically active corticosteroids. For example, they enable substituents to be introduced into the 9- and/or 11-position which can lead to a modification of the pharmacological activity.

In particular, the steroid-20-carboxylic acid halide is converted to the corresponding carboxylic acid azide, which in turn is transformed into the C-20-amine as described in my copending U.S. patent application Ser. No. 262,967, filed May 12, 1981.

The compounds of formula I where X represents a halide are reacted with a metal azide in an aqueous/organic two-phase reaction at a temperature of below about 25° C. and the resulting carboxylic acid azide is further processed by a reaction selected from the group consisting of:

(a) recovery of the azide and heating to give the C-20-isocyanate by the elimination of nitrogen and, optionally, the C-20-isocyanate thus obtained is converted into the C-20-carbamate or the C-20-amine, and (b) hydrolyzing the azide by heating in the presence of an aqueous acid with elimination of nitrogen into the C20-amine, and recovering said Δ4-C21-steroid compounds having the formula II:

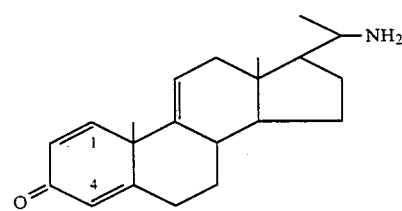

(II)

These compounds of formula II are useful for the production of steroid compounds having the acetyl side chain of progesterone in accordance with the following scheme:

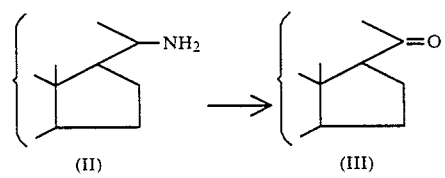

The method described in U.S. Pat. No. 4,252,732 for converting the 20-amino group to the 20-oxo group can be followed in all instances. The method described by patentee in Example 1 can be applied to the compounds of formula II. The compound of formula III, pregna-1,4,9(11)-trien-3,20-dione is described in U.S. Pat. No. 3,028,383 as the starting material for the synthesis of 9α-halo-11β-oxygenated-1,2-dehydroprogesterones which are useful, for example, in the treatment of rheumatic arthritis.

The conversion of the 20-amine to the 20-keto effected by the agency of 3,5-di-tert.-butyl-1-benzoquinone according to Example 1 of U.S. Pat. No. 4,252,732 can be applied to the above compounds of formula II.

Pregna-1,4,9(11)-trien-3,20-dione(III) can be transformed, in analogy to the process of Hogg et al., J. Am. Chem. Soc., 77, 4438 (1955) into 17(20)-en-21-carboxylated steroids:

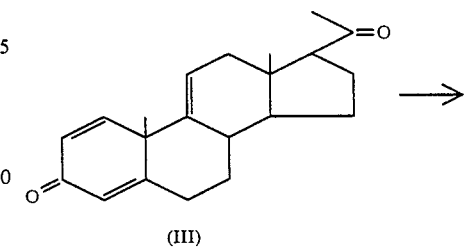

(III)

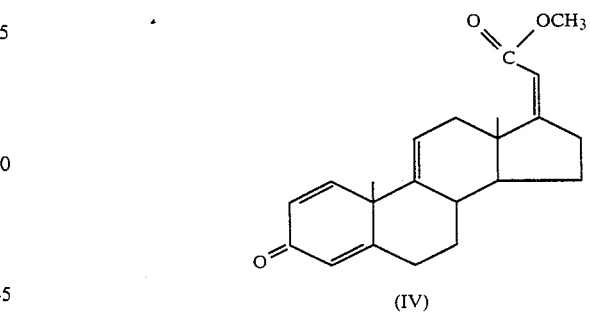

(IV)

The ester IV and the corresponding free acid are shown in U.S. Pat. No. 2,793,208 (C.A. 52, 464e) to be starting materials for the synthesis of corticoid hormones such as 9α-fluorinated prednisolone derivatives.

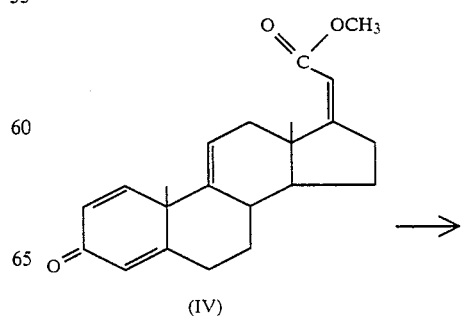

(IV)

(V)

The carboxylamide of the formula can be reacted with lead tetraacetate in tetrahydrofurane and hydrolysed according to U.S. Pat. Nos. 4,225,345 and 4,252,730 to give an amine having the formula The following examples are illustrative of the practice of the invention without being limitative in any respect.

EXAMPLE 1

Pregna-1,4,9(11)-triene-3-one-20-carbonyl chloride 0.3 ml of dry pyridine and 0.6 ml of thionyl chloride freshly distilled over squalene are added at 0° C. to 718 mg of 11-⊕-hydroxy-pregna-1,4-diene-3-one-20-carboxylic acid in 20 ml of dry $CH_2Cl_2$. After 1 hour at 0° C., the reaction product is concentrated in vacuo to dryness. The still greasy residue is redissolved in a little methylene chloride and the resulting solution again concentrated to dryness.

An IR-spectrum of the residue in $CHCl_3$ shows that conversion into the carboxylic acid chloride is complete (bands at 1777, 1665, 1638 (shoulder), 1628, 1609 cm$^{-1}$).

The crude pregna-1,4,9(11)-triene-3-one-20-carbonyl chloride thus obtained may be further reacted without purification. The yield is best determined after esterification of the acid chloride.

EXAMPLE 2

Determining the yield of pregna-1,4,9(11)-triene-3-one-20-carbonyl chloride obtained in accordance with example 1 by conversion into the methyl ester (pregna-1,4,9(11)-triene-3-one-20-carbonyl acid methyl ester)

The crude acid chloride obtained in accordance with example 1 from 718 mg of the acid is dissolved in 15 ml of dry methylene chloride, followed by the addition of 0.6 ml of pyridine and 2 ml of methanol. After 1 hour, the reaction mixture is diluted with 20 ml of $CH_2Cl_2$ and the organic phase is successively washed with water, dilute $H_2SO_4$ and again with water, subsequently dried and finally concentrated, leaving as residue 700 mg of the crude tri-unsaturated methyl ester.

The $^1H$-NMR-spectrum confirms the postulated structure. Quantitative thin-layer chromatography shows a yield of 86 percent based on the acid used.

$^1H$-NMR (80 MHz, $CDCl_3$ δ-values): 0.70 (18-$CH_3$, s), 1.17 (21-$CH_3$, dJ=6.9 Hz), 1.40 (19-$CH_3$, s), 3.64 (—$OCH_3$, s), 5.48 (11-CH), ABC-system of 1-CH, 2-CH, 3-CH: 6.05, 6.18, 6.20, 6.31, 6.33, 7.11, 7.23

EXAMPLE 3

Pregna-1,4,9(11)-triene-3-one-20-carboxamide

Pregna-1,4,9(11)-triene-3-one-20-carbonyl chloride obtained in accordance with example 1 from 718 mg of 11-β-hydroxy-pregna-1,4-diene-3-one-20-carboxylic acid is dissolved in 20 ml of dry $CH_2Cl_2$. Gaseous $NH_3$ is slowly passed through the solution over a period of 2 hours at 0° C., after which the solution is poured into the same quantity of ice water, followed by careful acidification with dilute hydrochloric acid.

After phase separation, the aqueous phase is washed twice with methylene chloride and the combined $CH_2Cl_2$-phases are dried over $Na_2SO_4$. Removal of the drying agent and concentration of the solvent leaves 650 mg of a solid from which 500 mg of the required amide are obtained by chromatography over silica gel (eluent: $CH_2Cl_2$ (85), ethyl acetate (10) and ethanol (5)).

$^1H$-NMR (80 MHz, $CDCl_3$, δ-values): 0.71 (18-$CH_3$, s), 1.20 (21-$CH_3$, dJ=6.4 Hz), 1.40 (19-$CH_3$), 5.48 (11-CH), ABC-system of 1-CH, 2-CH, 3-CH: 6.05, 6.18, 6.20, 6.31, 6.33, 7.12, 7.25.

I claim:

1. Δ1,4,9(11)-pregnatrien-3-ohne-20-carboxylic acid compounds corresponding to formula I below:

(I)

in which X is selected from the group consisting of halogen and $NH_2$.

2. Compounds as claimed in claim 1 in which X is selected from the group consisting of chlorine and bromine.

3. A process for the production of Δ1,4,9(11)-pregna-3-one-20-carboxylic acid compounds of claim 1 in which X is halogen which consists essentially of dehydrating structurally similar steroid-20-carboxylic acid starting materials saturated in the 9(11)-position and hydroxylated in the 11β-position by reacting with a halogenating agent at temperatures not exceeding 15° C. to form the 9(11)-ene bond and recovering said compounds of claim 1 where X is halogen.

4. A process as claimed in claim 3 in which the reaction of the steroid-20-carboxylic acid with the halogenating agent takes place at a temperature not exceeding 5° C.

5. A process as claimed in claim 3 or 4 in which a thionyl halide is used as the halogenating agent.

6. A process as claimed in claim 5 in which the thionyl halide is thionyl chloride.

7. A process as claimed in claim 3 in which the 9(11) dehydration step and formation of the steroid-20-carboxylic acid halide are carried out in a single stage by using the halogenating agent in an excess over and above the quantity required for forming the carboxylic acid halide.

8. A process as claimed in claim 7 in which an approximately 1 to 1.5 molar excess of halogenating agent is used.

9. A process as claimed in claim 5 in which the 9(11) dehydration step and formation of the steroid-20-carboxylic acid halide are carried out in a single stage by using the halogenating agent in an excess over and above the quantity required for forming the carboxylic acid halide.

10. A process as claimed in claim 9 in which an approximately 1 to 1.5 molar excess of halogenating agent is used.

11. A process for the production of Δ1,4,9(11)-pregna-3-one-20-carboxylic acid compounds of claim 1 in which X is $NH_2$, which consists essentially of dehydrating structurally similar steroid-20-carboxylic acid starting materials saturated in the 9(11)-position and hydroxylated in the 11β-position by reacting with a halogenating agent at temperatures not exceeding 15° C. to form the 9(11)-ene bond, reacting the steroid-20-carboxylic acid halide formed with an aminating agent selected from the group consisting of ammonia, an ammonia-yielding compound under the reaction conditions, and mixtures thereof at temperatures of about −20° C. to about 80° C., and recovering said compound of claim 1 where X is $NH_2$.

* * * * *